(12) United States Patent
Puterka et al.

(10) Patent No.: US 9,714,425 B2
(45) Date of Patent: Jul. 25, 2017

(54) DOUBLE STRANDED RNA CONSTRUCTS FOR APHID CONTROL

(71) Applicant: The United States of America, as represented by the Secretary of Agriculture, Washington, DC (US)

(72) Inventors: Gary J. Puterka, Stillwater, OK (US); Scott J. Nicholson, Perkins, OK (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 0 days.

(21) Appl. No.: 15/402,317

(22) Filed: Jan. 10, 2017

(65) Prior Publication Data
US 2017/0145422 A1 May 25, 2017

Related U.S. Application Data

(62) Division of application No. 14/825,427, filed on Aug. 13, 2015, now Pat. No. 9,580,709.

(60) Provisional application No. 62/040,714, filed on Aug. 22, 2014.

(51) Int. Cl.
| | | |
|---|---|---|
| C07H 21/02 | (2006.01) |
| C07H 21/04 | (2006.01) |
| C12N 15/113 | (2010.01) |
| A01N 25/00 | (2006.01) |
| A01N 57/16 | (2006.01) |
| A01N 25/02 | (2006.01) |
| C12N 5/00 | (2006.01) |

(52) U.S. Cl.
CPC ........ *C12N 15/1137* (2013.01); *A01N 25/006* (2013.01); *A01N 25/02* (2013.01); *A01N 57/16* (2013.01); *C12N 2310/14* (2013.01)

(58) Field of Classification Search
None
See application file for complete search history.

(56) References Cited

FOREIGN PATENT DOCUMENTS

WO   WO2006027571   3/2006

OTHER PUBLICATIONS

Bhatia et al.; Host Generated siRNAs Attenuate Expression of Serine Protease Gene in Myzus persicae, PLOS ONE; 2012, containing 9 pages, 7(10): e46343. doi:10.1371/journal.pone.0046343.
Whyard et al.; Ingested double-stranded RNAs can act as species-specific insecticides, Insect Biochemistry and Molecular Biology 39 (2009) 824-832.

*Primary Examiner* — Sean McGarry
(74) *Attorney, Agent, or Firm* — John D. Fado; Mark D. McNemar

(57) ABSTRACT

Disclosed are specific aphid dsRNA constructs that target either Chloride Intracellular Channel (CLIC) gene expression or Sucrase gene expression. Also disclosed is the use of dsRNA constructs of a CLIC gene to interfere with critical functions of CLIC gene peptide products. A novel method to develop nucleic acid control for pest management is also disclosed. Also disclosed is the use of dsRNA constructs to interfere with critical functions of Sucrase gene peptide products.

10 Claims, 12 Drawing Sheets

SEQUENCE LISTING

<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: CLIC-F primer

<400> SEQUENCE: 1
tggtaatggg cacgaagaa                                                      19

<210> SEQ ID NO 2
<211> LENGTH: 19
<212> TYPE: DNA
<213> ORGANISM: Artificial Sequence
<220> FEATURE:
<223> OTHER INFORMATION: CLIC-R primer

<400> SEQUENCE: 2
aatcgggagg aggttttttg                                                     19

<210> SEQ ID NO 3
<211> LENGTH: 43
<212> TYPE: DNA
<213> ORGANISM: Artificial Sequence
<220> FEATURE:
<223> OTHER INFORMATION: T7_CLIC-F primer

<400> SEQUENCE: 3
taatacgact cactataggg agaatggtaa tgggcacgaa gaa                            43

<210> SEQ ID NO 4
<211> LENGTH: 43
<212> TYPE: DNA
<213> ORGANISM: Artificial Sequence
<220> FEATURE:
<223> OTHER INFORMATION: T7_CLIC-R primer

<400> SEQUENCE: 4
taatacgact cactataggg agaaaatcgg gaggaggttt ttg                            43

<210> SEQ ID NO 5
<211> LENGTH: 196
<212> TYPE: DNA
<213> ORGANISM: Artificial Sequence
<220> FEATURE:
<223> OTHER INFORMATION: sense strand of a 5' to 3' dsRNA product
      referred to as dsRNA-CLIC

<400> SEQUENCE: 5
atggtaatgg gcacgaagaa aatggacatg tgccggaaat tgagctcatc attaaggctt         60
caacaattga cggtcgacga aaaggagcat gtctattttg ccaagaatat ttcatggacc        120
tatatctact tgccgagcta aaaaccatca gtcttaaagt cactacagta gatatgcaaa        180
aacctcctcc cgattt                                                        196

<210> SEQ ID NO 6
<211> LENGTH: 20
<212> TYPE: DNA
<213> ORGANISM: Artificial Sequence
<220> FEATURE:
<223> OTHER INFORMATION: Sucrase-F primer

<400> SEQUENCE: 6

```
tcacgtacta tgccgacgag                                                       20

<210> SEQ ID NO 7
<211> LENGTH: 20
<212> TYPE: DNA
<213> ORGANISM: Artificial Sequence
<220> FEATURE:
<223> OTHER INFORMATION: Sucrase-R primer

<400> SEQUENCE: 7
gaagccacgt tccatttgtt                                                       20

<210> SEQ ID NO 8
<211> LENGTH: 43
<212> TYPE: DNA
<213> ORGANISM: Artificial Sequence
<220> FEATURE:
<223> OTHER INFORMATION: T7 Sucrase-F primer

<400> SEQUENCE: 8
taatacgact cactataggg agatcacgta ctatgccgac gag                             43

<210> SEQ ID NO 9
<211> LENGTH: 43
<212> TYPE: DNA
<213> ORGANISM: Artificial Sequence
<220> FEATURE:
<223> OTHER INFORMATION: T7_Sucrase-R primer

<400> SEQUENCE: 9
taatacgact cactataggg agagaagcca cgttccattt gtt                             43

<210> SEQ ID NO 10
<211> LENGTH: 192
<212> TYPE: DNA
<213> ORGANISM: Artificial Sequence
<220> FEATURE:
<223> OTHER INFORMATION: sense strand of a 5' to 3' dsRNA product
      referred to as dsRNA-Sucrase

<400> SEQUENCE: 10
tcacgtacta tgccgacgag ttgggtgtac aaaacacgta tgtccgatgg aaccaaactg           60
tggacccggc aggacgtaac gtcggtccat tgcggtacac gcaattcact agagatccag          120
ccagaactcc gtttccctgg aatgactctg aaaacgcagg ttttactaac ggaacaaatg          180
gaacgtggct tc                                                              192
```

DOUBLE STRANDED RNA CONSTRUCTS FOR APHID CONTROL

CROSS-REFERENCE TO RELATED APPLICATIONS

Figure 1A:
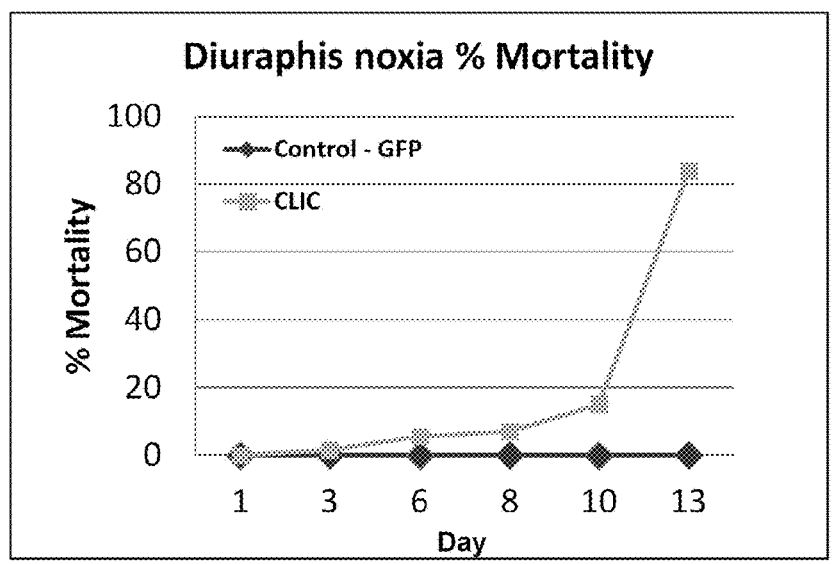
Figure 1B:
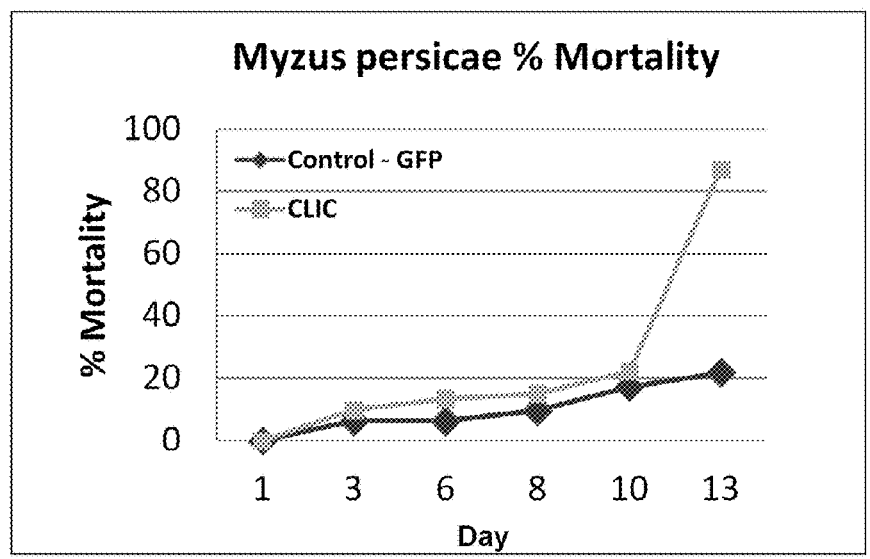
Figure 1C:
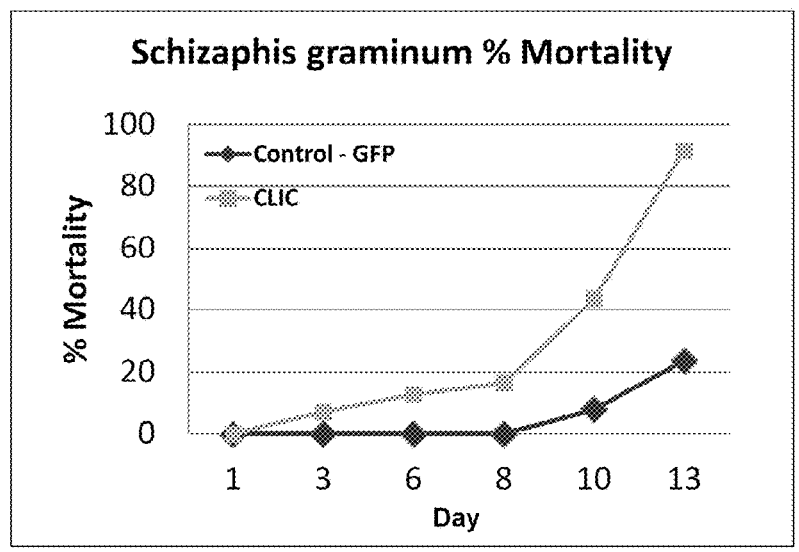
Figure 2A:
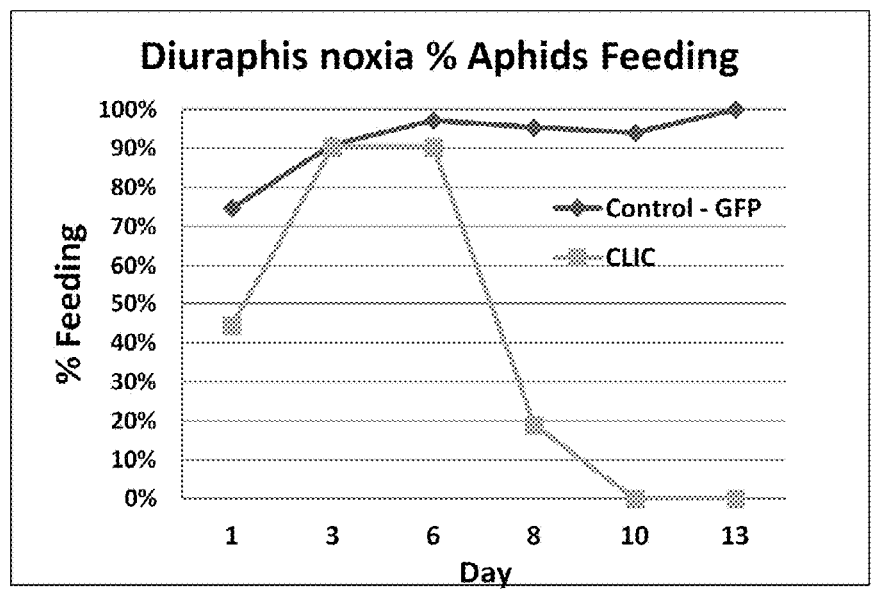
Figure 2B:
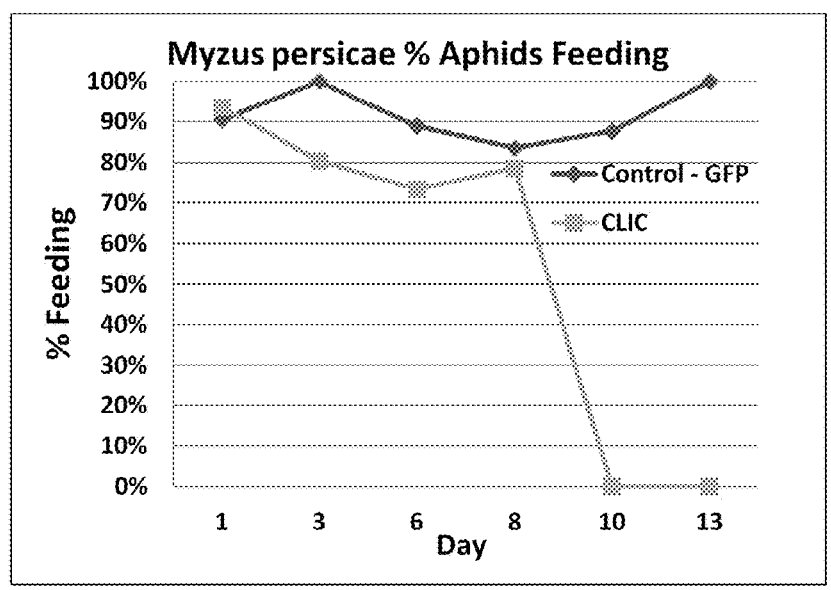
Figure 2C:
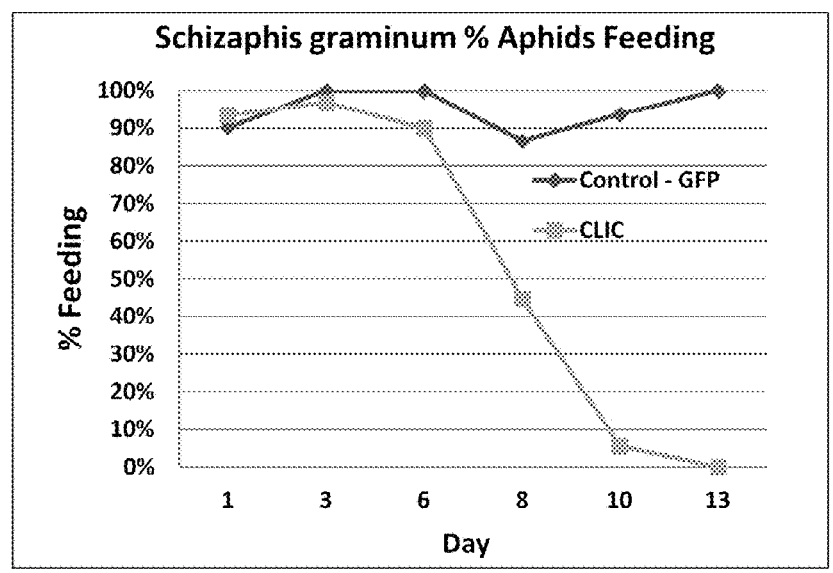
Figure 3A:
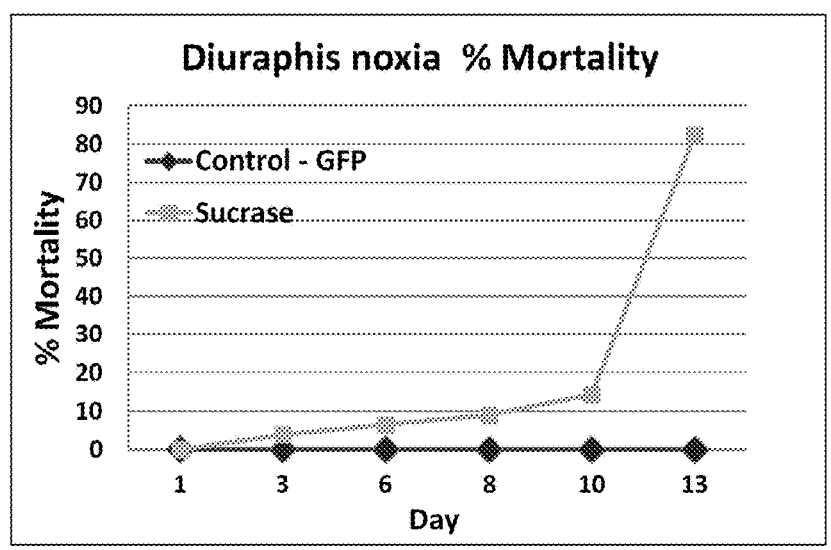
Figure 3B:
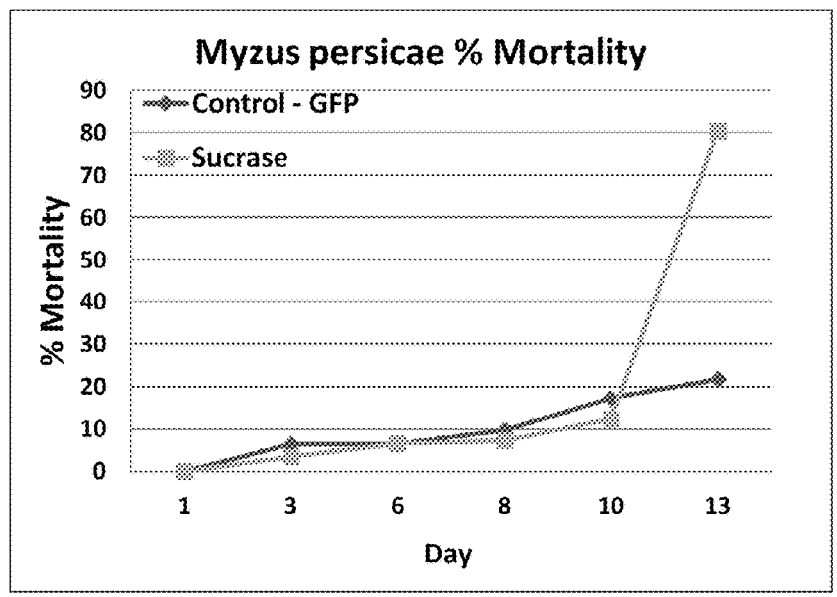
Figure 3C:
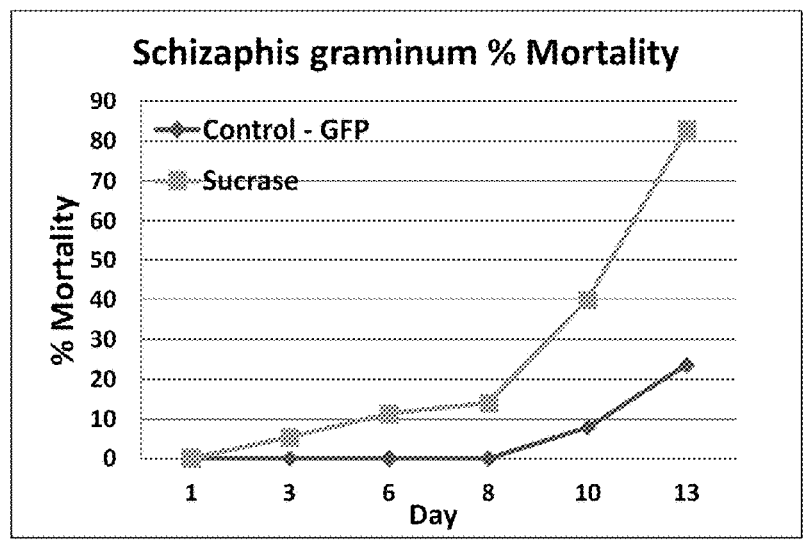
Figure 4A:
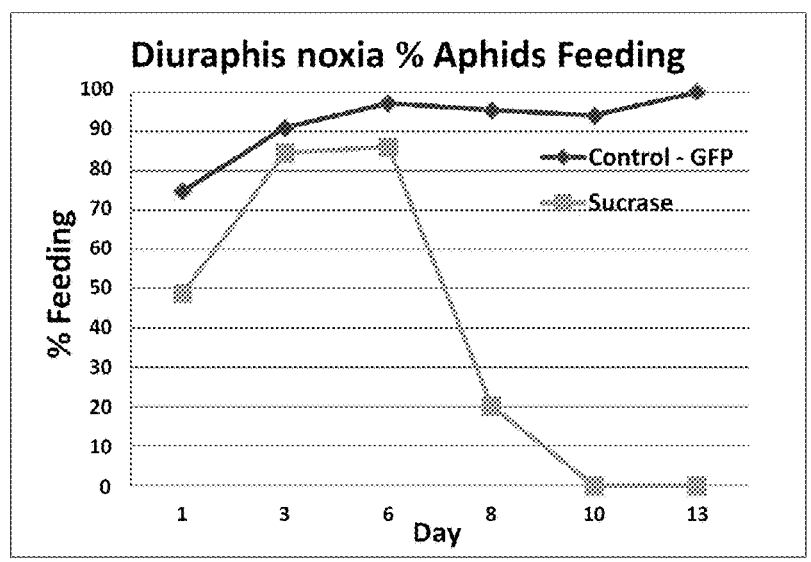
Figure 4B:
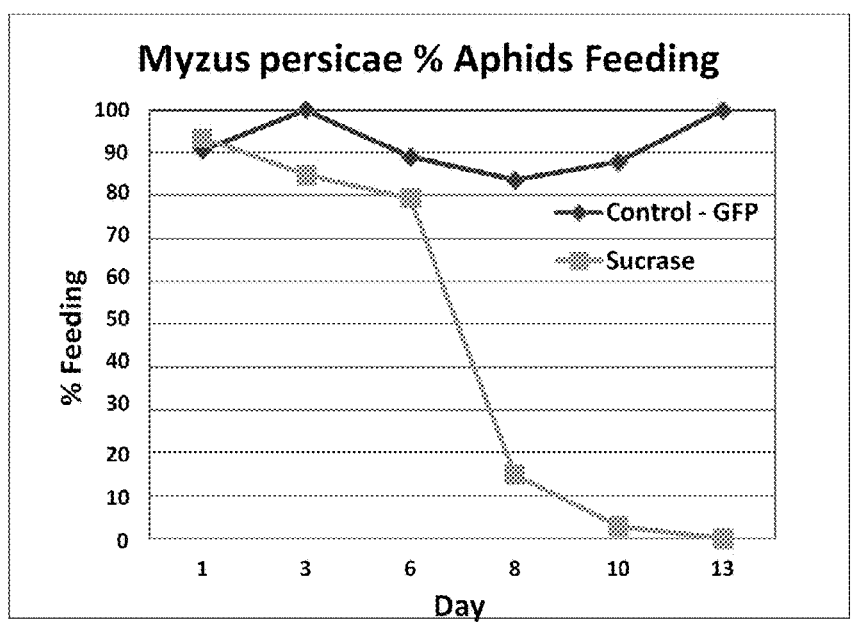
Figure 4C:
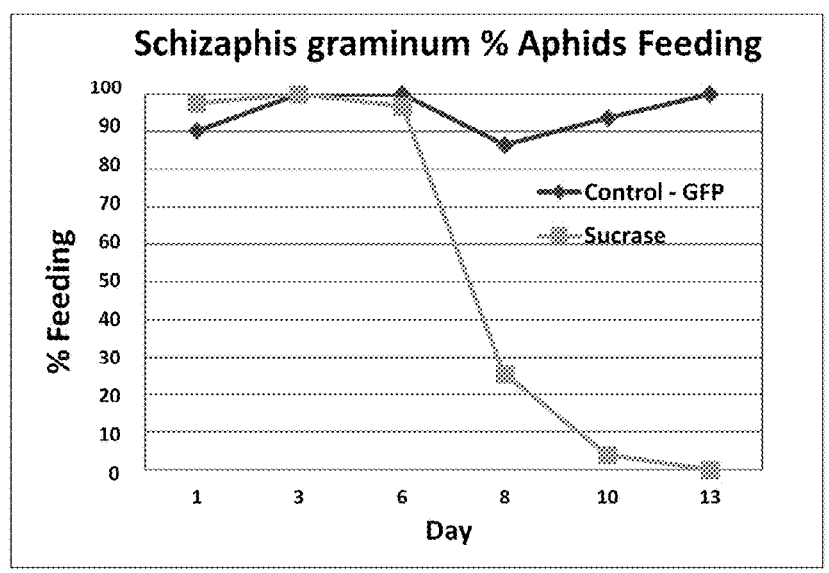

This application is a divisional of U.S. patent application Ser. No. 14/825,427, filed on Aug. 13, 2015, which claims priority under 35 U.S.C. §119(e) to U.S. Provisional Ser. No. 62/040,714, which was filed on Aug. 22, 2014, the contents of which are hereby incorporated by reference herein in their entirety.

FIELD OF THE INVENTION

This invention relates to double stranded RNA constructs to inhibit the expression of either Chloride Intracellular Channel protein (CLIC) or Sucrase to induce mortality in aphid species, including but not limited to *Diuraphis noxia*, *Myzus persicae*, and *Schizaphis graminum*.

BACKGROUND OF INVENTION

There are currently 5000 species of Aphididae with over 100 species economically important as pests of crops (Blackman & Eastop 2006, 2007). Aphids are phloem sap feeders that damage the plants through the removal of carbohydrates and amino acids and by injecting phytotoxic saliva and vectoring plant diseases while feeding. The Russian wheat aphid, *Diuraphis noxia*, and the greenbug, *Schizaphis graminum*, are globally distributed and significant pests of cereals, causing losses exceeding $250 million/year in the mid-western United States alone (Webster 1994, Morrison and Peairs 1998). *M. persicae* attacks over 200 species of plants and is known by many names including green peach aphid or peach-potato aphid. Plant damage occurs mainly from the aphid's transmission of viruses lethal to many vegetables and tobacco (Eastop 1977. Blackman and Eastop 2000). The low profit margins in crop production and frequent insecticide use required to mitigate losses caused by aphids are economically unsustainable.

Chemical pesticides such as pyrethrins and pyrethroids are the most common means of controlling aphids. However the use of traditional chemical pesticides has disadvantages, including non-target effects on neutral or beneficial insects, as well as other animals. Chemical pesticide usage also can lead to chemical residue run-off into streams and seepage into water supplies resulting in ecosystem/environment damage. In addition, animals higher in the food chain are at risk when they consume pesticide contaminated crops or insects. The handling and application of chemical pesticides also presents exposure danger to the public and professionals, and could lead to accidental dispersal into unintended environmentally sensitive areas. In addition, prolonged chemical pesticide application may result in an insect population becoming resistant to a chemical pesticide. In order to control a traditionally chemical resistant-pest, new more potent chemical pesticides must be utilized, which in turn will lead to another resistance cycle. As such, there is a need in the art to control pest populations without the disadvantages of traditional chemical pesticides.

An approach to decrease dependence on chemical pesticides is by causing a specific gene(s) of the target-pest to malfunction by either over expression or silencing gene expression. The silencing approach utilizes RNA interference pathways to knockdown the gene of interest via double stranded RNA. Double stranded RNA (dsRNA) induces sequence-specific post-transcriptional gene silencing in many organisms by a process known as RNA interference (RNAi). RNAi is a post-transcriptional, highly conserved process in eukaryotes that leads to specific gene silencing through degradation of the target mRNA. The silencing mechanism is mediated by dsRNA that is homologous in sequence to the gene of interest. The dsRNA is processed into small interfering RNA (siRNA) by an endogenous enzyme called DICER inside the target pest, and the siRNAs are then incorporated into a multi-component RNA-induced silencing complex (RISC), which finds and cleaves the target mRNA. The dsRNA inhibits expression of at least one gene within the target, which exerts a deleterious effect upon the target.

Fire, et al. (U.S. Pat. No. 6,506,559) discloses a process of introducing RNA into a living cell to inhibit gene expression of a target gene in that cell. The RNA has a region with double-stranded structure. Inhibition is sequence-specific in that the nucleotide sequences of the duplex region of the RNA and of a portion of the target gene are identical. Specifically, Fire, et al. (U.S. Pat. No. 6,506,559) discloses a method to inhibit expression of a target gene in a cell, the method comprising introduction of a double stranded ribonucleic acid into the cell in an amount sufficient to inhibit expression of the target gene, wherein the RNA is a double-stranded molecule with a first ribonucleic acid strand consisting essentially of a ribonucleotide sequence which corresponds to a nucleotide sequence of the target gene and a second ribonucleic acid strand consisting essentially of a ribonucleotide sequence which is complementary to the nucleotide sequence of the target gene. Furthermore, the first and the second ribonucleotide strands are separately complementary strands that hybridize to each other to form the said double-stranded construct, and the double-stranded construct inhibits expression of the target gene.

To utilize RNA interference as a method to regulate gene expression to control a target organism, a specific essential gene needs to be targeted. One such gene is the Chloride Intracellular Channel (CLIC) gene. The CLIC gene encodes a multifunctional protein thought to be involved in number of cellular processes based on its role in glutathione signaling and in allowing chloride ion flux across membranes (Averaimo, et al. 2010).

Another gene of interest is Sucrase. The Sucrase gene encodes a protein responsible for the hydrolysis of sucrose into fructose and glucose. Sucrose is the main plant sugar, and so is the most important sustenance for plant-feeding insects. Interference with an insect's ability to metabolize sucrose will thereby starve the insect (Karley, et al. 2005).

Such novel control methods that would induce silencing of CLIC and Sucrase would be desirable as they avoid the undesirable characteristics of traditional chemical pesticides. Traditional chemical pesticides in general have the disadvantage of being toxic to the environment as well as affecting a broad range of insect. To that end, there is a need to develop dsRNA constructs that are engineered to target and silence CLIC and Sucrase mRNA that would overcome some of the disadvantages of using traditional pesticides and that can target specific pests.

BRIEF SUMMARY OF THE INVENTION

Disclosed herein is a double-stranded ribonucleic acid (dsRNA) for inhibiting the expression of a Chloride Intracellular Channel protein in a cell, wherein said dsRNA comprises a sense strand comprising a first sequence and an antisense stand comprising a second sequence complementary to SEQ ID NO: 5, wherein said first sequence is complementary to said second sequence.

Also disclosed herein is a double-stranded ribonucleic acid (dsRNA) for inhibiting the expression of a Sucrase enzyme in a cell, wherein said dsRNA comprises a sense strand comprising a first sequence and an antisense stand comprising a second sequence complementary to SEQ ID NO: 10, wherein said first sequence is complementary to said second sequence.

Disclosed herewith is a method for controlling an aphid species, the method comprising: constructing a double stranded ribonucleic acid construct that is complementary to a gene that encodes a Chloride Intracellular Channel protein, dissolving the double stranded ribonucleic acid to form a solution, and contacting an effective amount of said solution to an aphid species, wherein said solution is ingested by said aphid and RNA interference is induced, resulting in mortality of said aphid.

In one embodiment of the invention, one strand of the double stranded ribonucleic acid is used to control the aphid, wherein the double stranded ribonucleic acid is complementary to the nucleotide sequence of SEQ ID NO: 5.

Disclosed herewith is a method for controlling an aphid species, the method comprising: constructing a double stranded ribonucleic acid construct that is complementary to a gene that encodes a Sucrase enzyme, dissolving the double stranded ribonucleic acid to form a solution, and contacting an effective amount of said solution to an aphid species, wherein said solution is ingested by said aphid and RNA interference is induced, resulting in mortality of said aphid.

In one embodiment of the invention, one strand of the double stranded ribonucleic acid is used to control the aphid, wherein the double stranded ribonucleic acid is complementary to the nucleotide sequence of SEQ ID NO: 10.

In another embodiment of the invention, the dsRNA construct disclosed herein was used to control aphid species that consist essentially of *Diuraphis noxia*, *Myzus persicae*, and *Schizaphis graminum*.

In another embodiment of the invention, the double stranded ribonucleic acid construct is dissolved in a sucrose solution. In yet another embodiment of the invention, the double stranded ribonucleic acid construct is dissolved in water.

In an embodiment of the invention, the double stranded ribonucleic acid construct is applied to aphid bait material. In various embodiments of the bait material, the bait material is a granular bait. In different embodiments of the bait material, the bait material can be a solution or granules that attract a target aphid.

In another embodiment of the invention, a double stranded ribonucleic acid construct is mixed with a solution, wherein the solution is applied topically to a plant control aphid.

It is contemplated that the dsRNA constructs disclosed herein can be delivered to a target aphid via plant-mediated delivery. An example of this would be a transgenic plant expressing the dsRNA construct in the plant parts the target aphid would ingest. Another contemplated RNAi construct delivery means includes spraying a plant with a solution of comprising the dsRNA construct. Other contemplated RNAi construct delivery means includes spraying the target aphid with a solution comprising the dsRNA construct wherein the solution penetrates the aphid cuticle and delivers the dsRNA construct in vivo. A contemplated example of this would be a surfactant solution comprising the dsRNA constructs disclosed herein. In another embodiment, it is contemplated that the dsRNA construct can be delivered via a virus-induced gene silencing (VIGS) for transient induction of silencing. (doi:10.1101/pdb.prot5139 *Cold Spring Harb Protoc* 2009).

BRIEF DESCRIPTION OF THE DRAWING

The present invention together with the disclosed embodiments may best be understood from the following detailed description of the drawings, wherein:

FIGS. 1A-C are graphs depicting mortality percentages of *Diuraphis noxia, Myzus persicae*, and *Schizaphis graminum* over a period of 13 days after liquid feeding assay initiated with in vitro synthesized dsRNA-CLIC construct compared with a control GFP dsRNA.

FIGS. 2A-C are graphs depicting reduced feeding time of *Diuraphis noxia, Myzus persicae*, and *Schizaphis graminum* over a period of 13 days after liquid feeding assay initiated with in vitro synthesized dsRNA-CLIC construct compared with a control GFP dsRNA.

FIGS. 3A-C are graphs depicting mortality percentages of *Diuraphis noxia, Myzus persicae*, and *Schizaphis graminum* over a period of 13 days after liquid feeding assay initiated with in vitro synthesized dsRNA-Sucrase construct compared with a control GFP dsRNA.

FIGS. 4A-C are graphs depicting reduced feeding time of *Diuraphis noxia, Myzus persicae*, and *Schizaphis graminum* over a period of 13 days after liquid feeding assay initiated with in vitro synthesized dsRNA-Sucrase construct compared with a control GFP dsRNA.

BRIEF DESCRIPTION OF THE SEQUENCES

SEQ ID NO: 1 is CLIC-F primer, TGGTAATGGGCACGAAGAA.

SEQ. ID NO: 2 is CLIC-R primer, AATCGGGAGGAGGTTTTTG.

SEQ. ID NO: 3 is T7_CLIC-F primer, TAATACGACTCACTATAGGGAGAATGGTAATGGGCACGAAGAA.

SEQ. ID NO: 4 is T7_CLIC-R primer, TAATACGACTCACTATAGGGAGAAAATCGGGAGGAGGTTTTTG.

SEQ. ID NO 5 is the sense strand of a 5' to 3' dsRNA product referred to as dsRNA-CLIC: ATGGTAATGGGCACGAAGAAAATGGACATGTGCCGGAAATTGAGCTCATCATTAAG GCTTCAACAATTGACGGTCGACGAAAAGGAGCATGTCTATTTTGCC AAGAATATTTC ATGGACCTATATCTACTTGCCGAGCTAAAAACCATCAGTCTTAAAGTCACTACAGTA GATATGCAAAAACCTCCTCCCGATTT.

SEQ. ID NO: 6 is Sucrase-F primer, TCACGTACTATGCCGACGAG.

SEQ. ID NO: 7 is Sucrase-R primer, GAAGCCACGTTCCATTTGTT.

SEQ. ID NO: 8 is T7_Sucrase-F primer, TAATACGACTCACTATAGGGAGATCACGTACTATGCCGACGAG.

SEQ. ID NO: 9 is T7_Sucrase-R primer, TAATACGACTCACTATAGGGAGAGAAGCCACGTTCCATTTGTT.

SEQ. ID NO: 10 is the sense strand of a 5' to 3' dsRNA product referred to as dsRNA-Sucrase: TCACGTACTATGCCGACGAGTTGGGTGTACAAAACACGTATGTCCGATGGAACCAA ACTGTGGACCCGGCAGGACGTAACGTCGGTCCATTGCGGTACACGCAATTCACTAG AGATCCAGCCAGAACTCCGTTTCCCTGGAATGACTCTGAAAACGCAGGTTTTACTAA CGGAACAAATGGAACGTGGCTTC.

DETAILED DESCRIPTION OF THE INVENTION

Disclosed are specific aphid dsRNA constructs that target either Chloride Intracellular Channel (CLIC) gene expression or Sucrase gene expression. Also disclosed is the use of dsRNA constructs of a CLIC gene to interfere with critical functions of CLIC gene peptide products. A novel method to develop nucleic acid control for pest management is also disclosed. Also disclosed is the use of dsRNA constructs to interfere with critical functions of Sucrase gene peptide products.

Definitions

As used in the specification and claims, the singular form "a", "an" and "the" include plural references unless the context clearly dictates otherwise. For example, the term "a cell" includes a plurality of cells, including mixtures thereof.

The term "gene" refers to a DNA sequence involved in producing a polypeptide or precursor thereof. The polypeptide can be encoded by a full-length coding sequence or by any portion of the coding sequence, such as exon sequences.

The term "oligonucleotide" refers to a molecule comprising a plurality of deoxyribonucleotides or ribonucleotides. Oligonucleotide may be generated in any manner, including chemical synthesis, DNA replication, reverse transcription, polymerase chain reaction, or a combination thereof. The present invention embodies utilizing the oligonucleotide in the form of dsRNA as means of interfering with native gene expression that leads to control of the target insect. Inasmuch as mononucleotides are synthesized to construct oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide, which is capable of acting as a point of initiation of synthesis when placed under conditions in which primer extension is initiated. An oligonucleotide "primer" may occur naturally, as in a purified restriction digest or may be produced synthetically.

A primer is selected to be "substantially complementary" to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence is sufficiently complementary with the sequence of the template to hybridize and thereby form a template primer complex for synthesis of the extension product of the primer.

The term "double stranded RNA" or "dsRNA" refers to two substantially complementary strands of ribonucleic acid. "Identity," as used herein, is the relationship between two or more polynucleotide sequences, as determined by comparing the sequences. Identity also means the degree of sequence relatedness between polynucleotide sequences, as determined by the match between strings of such sequences. Identity can be readily calculated (see, e.g, *Computation Molecular Biology*, Lesk, A. M., eds., Oxford University Press, New York (1998), and *Biocomputing: Informatics and Genome Projects*, Smith, D. W., ed., Academic Press, New York (1993), both of which are incorporated by reference herein). While there exist a number of methods to measure identity between two polynucleotide sequences, the term is well known to skilled artisans (see, e.g., *Sequence Analysis in Molecular Biology*, von Heinje, G., Academic Press (1987); and *Sequence Analysis Primer*, Gribskov., M. and Devereux, J., eds., M Stockton Press, New York (1991)). Methods commonly employed to determine identity between sequences include, for example, those disclosed in Carillo, H., and Lipman, D., *SIAM J. Applied Math*. (1988) 48:1073. "Substantially identical" as used herein, means there is a very high degree of homology (preferably 100% sequence identity) between the inhibitory dsRNA and the corresponding part of the target gene. However, dsRNA having greater than 90% or 95% sequence identity may be used in the present invention, and thus sequence variations that might be expected due to genetic mutation, strain polymorphism, or evolutionary divergence can be tolerated. Although 100% identity is preferred, the dsRNA may contain single or multiple base pair random mismatches between the RNA and the target gene, provided that the mismatches occur at a distance of at least three nucleotides from the fusion site.

As used herein, "target gene" refers to a section of a DNA strand of a double-stranded DNA that is complementary to a section of a DNA strand, including all transcribed regions, that serves as a matrix for transcription. The target gene is therefore usually the sense strand.

The term "complementary RNA strand" refers to the strand of the dsRNA, which is complementary to an mRNA transcript that is formed during expression of the target gene, or its processing products. "dsRNA" refers to a ribonucleic acid molecule having a duplex structure comprising two complementary and anti-parallel nucleic acid strands. Not all nucleotides of a dsRNA must exhibit Watson-Crick base pairs. The maximum number of base pairs is the number of nucleotides in the shortest strand of the dsRNA.

"Small interfering RNA" or "siRNA" refers to a short double-strand of ribonucleic acid, approximately 18 to 200 nucleotides in length. The term "RNA interference" or "RNAi" refers to a cellular mechanism for the destruction of targeted ribonucleic acid molecules. Under endogenous conditions, RNAi mechanism operates when dsRNA is cleaved to siRNA via an enzyme, DICER. The siRNA is processed to a single strand of anti-sense ribonucleic acid and coupled with a protein complex named RISC. The antisense RNA then targets a complementary gene construct, such as messenger RNA that is cleaved by ribonuclease. While the examples infra discloses constructing dsRNA constructs via enzymatic techniques with the enzyme RNA polymerase, it is contemplated that siRNA can be constructed via RNA oligonucleotide synthesis such as those disclosed in Scaringe, S., Methods Enzymol., 2000, Vol. 317:3 and incorporated herein by reference.

Disclosed herein are long dsRNA constructs, such as the SEQ ID NOS: 5 and 10. It is contemplated that siRNA and/or partial dsRNA sequences from those sequence listings constructs comprising various double-stranded base pairs of disclosed long dsDNA constructs would be effective in knocking-down the gene function in a target aphid species. It is contemplated that such siRNA and/or partial dsRNA sequences from SEQ ID NOS: 5 and 10 could be generated synthetically or enzymatically in accordance with the teachings herein.

As used herein, "knock-down" is defined as the act of binding an oligonucleotide with a complementary nucleotide sequence of a gene as such that the expression of the gene or mRNA transcript decreases.

The term "substantially single-stranded" when used in reference to a nucleic acid product means that the product molecule exists primarily as a single strand of nucleic acid in contrast to a double-stranded product which exists as two strands of nucleic acids which are held together by interstrand base pairing interactions.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like.

The term "corresponds to" as used herein means a polynucleotide sequence homologous to all or a portion of a reference polynucleotide sequence, or a polypeptide sequence that is identical to a reference polypeptide sequence. In contradistinction, the term "complementary to" is used herein to mean that the complementary sequence is homologous to all or a portion of a reference polynucleotide sequence. For example, the nucleotide sequence "TATAC" corresponds to a reference sequence "TATAC" and is complementary to a reference sequence "GTATA".

An "effective amount" is an amount sufficient to effect desired beneficial or deleterious results. An effective amount can be administered in one or more administrations. In terms of treatment, an "effective amount" is that amount sufficient to make the target pest non-functional by causing an adverse effect on that pest, including (but not limited to) physiological damage to the pest; inhibition or modulation of pest growth; inhibition or modulation of pest reproduction; or death of the pest. In one embodiment of the invention, a dsRNA containing solution is fed to a target insect in an amount of approximately at a concentration of 314 ng/µl of solution. An effective amount include amounts less that that concentration in which pest mortality would still occur.

The term "solvent" includes any liquid that holds another substance in solution. Examples of solvents include but are not limited to water and organic solvents such as acetone, ethanol, dimethyl sulfoxide (DMSO), and dimethylformamide (DMF).

As used herein, the term "GFP dsRNA" refers to a control dsRNA construct. The green fluorescent protein (GFP) is commonly used as a reporter gene and was originally isolated from jellyfish and widely used as control in prokaryotic and eukaryotic systems.

The term "phagostimulant" refers to any substance that will entice the insect to ingest the dsRNA. For insects, suitable phagostimulants include but are not limited to edible oils and fats, vegetable seed meals, meal by-products such as blood, fish meal, syrups, honey, aqueous solutions of sucrose, artificial sweeteners such as sucralose, saccharin, and other artificial sweeteners, peanut butter, cereals, amino acids, and other proteins. Sucrose is a will known feeding stimulant for aphids.

Methods which are well known to those skilled in the art may be used to construct expression vectors containing sequences encoding Guanine nucleotide binding protein gene and appropriate transcriptional and translational control elements. These methods include in vitro recombinant DNA techniques, synthetic techniques, and in vivo genetic recombination. Such techniques are described in Sambrook, J. et al. (2001) *Molecular Cloning, A Laboratory Manual*, Cold Spring Harbor Press, Plainview, N.Y., and Ausubel, F. M. et al. (2001) Current Protocols in Molecular Biology, John Wiley & Sons, New York, N.Y.

While the examples provided herein describe dsRNA constructs cloned from GenBank Accession No. JOTR00000000 it is contemplated that when read in conjunction with the teaching disclosed herein, the construction of other dsRNA constructs targeting CLIC or Sucrase gene sequences of other insect orders would be feasible to those skilled the in the art. Additionally it is contemplated that a single dsRNA construct would be effective in controlling a plurality of insect species.

Aphid colonies used in the foregoing examples originated from field collections held at USDA, ARS, Stillwater, Okla. The biotype E greenbug and Russian wheat aphid biotype 2 (RWA2) were both reared on 'Yuma' wheat 6 months prior to tests. *Myzus persicae* was reared on a mixture of 'Long Island Imperial' brussel sprouts and 'Southern Giant' mustard. Aphid host plants were grown potting soil in 8 cm diameter pots covered by ventilated cylindrical clear plastic cages. Aphid infested plants were held in a room with temperatures of 20-22° C. on light racks with a 14:10 L:D photoperiod provided by four 40 w cool white fluorescent lights. As referred to herein, "RWA" refers to the Russian wheat aphid. It is contemplated that the dsRNA constructs disclosed herein would have broad aphid activity against aphids, a large range of taxonomically distant aphid species including but not limited to: the greenbug, *Schizaphis graminum*; green peach aphid, *Myzus persicae*; Russian wheat aphid, *Diuraphis noxia*; pea aphid, *Acyrthosiphon pisum*; soybean aphid, *Aphis glycines*; and bird cherry-oat aphid, *Rhopalosiphum padi*.

Example 1: Constructing dsRNA Construct for Aphid Species

Cloning and Sequencing of the CLIC Gene

The CLIC gene was identified by comparing RNA expressed by RWA, as determined by RNAseq expression data, to the RWA whole genome sequence. The CLIC mRNA sequence was identified and primers were created for its amplification and for production of sequence-specific dsRNA. To create dsRNA specifically targeting the RWA CLIC sequence, whole RNA was isolated from 50 adult RWA biotype 2 aphids using the Promega SV total RNA isolation kit. Aphids were ground together in liquid nitrogen and RNA extraction proceeded according to protocol. Total RNA was eluted in RNAse-free water (Promega), DNAse-treated (Ambion DNA-free kit), and quantified and assessed for purity using a spectrophotometer (A260). RNA aliquots were stored at −80° C. cDNA of CLIC was amplified from total RNA using first-strand synthesis with gene-specific reverse primer (CLIC-R (Seq 2)) (Agilent Affinity-script Multi-Temperature cDNA synthesis kit). The first-strand synthesis reaction was then used as a template for end-point PCR using the full (CLIC-F(Seq 1) and CLIC-R (Seq2)) primer set. The full-length PCR product for CLIC was then gel-purified (Promega SV Gel and PCR Clean-up System) and subjected to PCR using primers with attached T7 RNA polymerase promoters (T7_CLIC-F(Seq 3) and T7_CLIC-R (Seq 4)). This fragment, which possessed T7 RNA polymerase promoters on each 5' end (sense and antisense strand), was gel-purified and stored at −80° C.

Construction of CLIC dsRNA Constructs

The T7-containing CLIC fragments generated as described in the passage above were used as a template to generate double-stranded RNA after spectrophotometric quantification (A260). 200 ng of the CLIC T7 template was used in each reaction to generate dsRNA copies of CLIC with the Ambion Megascript in vitro transcription kit. The reactions were allowed to proceed for 16 hours at 37° C. and the resulting product was column purified with Ambion Nuc-Away columns, quantified spectrophotometrically (A260) and visualized on an agarose gel to assess purity and concentration. The isolated dsRNA was then stored at −80° C. for preservation until further use.

Example 2: dsRNA Construct Feeding Bioassay Using Liquid Bait Station

All aphid species were fed upon the same artificial diet consisting of 15% sucrose solution in water amended with a 2% amino acid solution ('Complete Amino Acid Mix', Nutricia North America, Rockville, Md.) and addition of 314 ng per µl of each dsRNA. The dsRNA treatments were mixed within the artificial diet at a concentration of 314 ng per µl for CLIC. The dsRNA treated and null control diets were contained in feeding stations consisting of a 35 mm diam. petri dish 10 mm deep×35 with 50 ul of diet sandwiched between two layers of stretched parafilm. A 15 mm rubber o-ring was placed over the diet area, 20-30 aphids were placed on the diet within the ring, and sealed within the o-ring by the petri dish lid held in place with parafilm. This feeding station allowed the aphids to move and feed freely for up to 15 d. The clear plastic lid that sealed the aphids on the diet allowed aphid and mobility counts to be made without lid removal. The toxicity of CLIC dsRNAs was determined by percent mortality, and the number of aphids actively feeding was compared between dsRNA treatments and null controls every two days up to 13 d post infestation. Unsettled/agitated aphids that were not actively feeding usually died within 7 d after being placed on successful dsRNA constructs that showed activity against aphids versus other dsRNA constructs that had no activity.

Example 3: Constructing dsRNA Construct for Aphid Species

Cloning and Sequencing of Sucrase Gene

The Sucrase gene was identified by comparing expressed RNA in RWA, as determined by RNAseq expression data, to the RWA whole genome sequence. The Sucrase mRNA sequence was identified and primers were created for its amplification and for production of sequence-specific dsRNA. To create dsRNA specifically targeting the RWA Sucrase sequence, whole RNA was isolated from 50 adult RWA biotype 2 aphids using the Promega SV total RNA isolation kit. Aphids were ground together in liquid nitrogen and RNA extraction proceeded according to protocol. Total RNA was eluted in RNAse-free water (Promega), DNAse-treated (Ambion DNA-free kit), and quantified and assessed for purity using a spectrophotometer (A260). RNA aliquots were stored at −80° C. cDNA of Sucrase was amplified from total RNA using first-strand synthesis with gene-specific reverse primer (Sucrase-R (Seq7)) (Agilent Affinity-script Milti-Temperature cDNA synthesis kit). The first-strand synthesis reaction was then used as a template for end-point PCR using the full (Sucrase-F (SEQ 6) and Sucrase-R (SEQ7)) primer set. The full-length PCR product for Sucrase was then gel-purified (Promega SV Gel and PCR Clean-up System) and subjected to PCR using primers with attached T7 RNA polymerase promoters (T7_Sucrase-F (SEQ8) and T7_Sucrase-R (SEQ 9)). This fragment, which possessed T7 RNA polymerase promoters on each 5' end (sense and antisense strand) was gel-purified and stored at −80° C.

Construction of Sucrase dsRNA Constructs

The T7-containing Sucrase fragments generated as described in the passage above were used as a template to generate double-stranded RNA after spectrophotometric quantification (A260). 200 ng of the Sucrase T7 template was used in each reaction to generate dsRNA copies of Sucrase with the Ambion Megascript in vitro transcription kit. The reactions were allowed to proceed for 16 hours at 37° C. and the resulting product was column purified with Ambion Nuc-Away columns, quantified spectrophotometrically (A260) and visualized on an agarose gel to assess purity and concentration. The isolated dsRNA was then stored at −80° C. for preservation until further use.

Example 4: dsRNA Construct Feeding Bioassay Using Liquid Bait Station

All aphid species were fed upon the same artificial diet consisting of 15% sucrose solution in water amended with an amino acid solution containing 314 ng per µl of Sucrase dsRNA. The dsRNA treatments were mixed within the artificial diet at a concentration of 314 ng per µl for Sucrase. The dsRNA treated and null control diets were contained in feeding stations consisting of a 35 mm diam. petri dish 10 mm deep×35 with 50 ul of diet sandwiched between two layers of stretched parafilm. A 15 mm rubber o-ring was placed over the diet area, 20-30 aphids were placed on the diet within the ring, and sealed within the o-ring by the petri dish lid held in place with parafilm. This feeding station allowed the aphids to move and feed freely for up to 15 d. The clear plastic lid that sealed the aphids on the diet allowed aphid and mobility counts to be made without lid removal. The toxicity of Sucrase dsRNA was determined by percent mortality, and the numbers of aphids actively feeding were compared between Sucrase dsRNA treatments and null controls every two days up to 13 d post infestation. Unsettled/agitated aphids that were not actively feeding usually died within 7 d after being placed on successful dsRNA constructs that showed activity against aphids versus other dsRNA constructs that had no activity.

To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2 d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

While the invention has been described with reference to details of the illustrated embodiment, these details are not intended to limit the scope of the invention as defined in the appended claims. All cited references and published patent applications cited in this application are incorporated herein by reference. The embodiment of the invention in which exclusive property or privilege is claimed is defined as follows:

The invention claimed is:

1. A double-stranded ribonucleic acid (dsRNA) for inhibiting the expression of a gene encoding a sucrase enzyme in a cell, wherein said dsRNA comprises a first strand comprising a sequence with at least 95% sequence identity to a portion of at least 18 consecutive nucleotides of SEQ ID NO: 10 and a second strand complementary to the first strand.

2. A method for controlling an aphid, the method comprising: constructing a double stranded ribonucleic acid (dsRNA) wherein one strand of the dsRNA comprises a sequence with at least 95% sequence identity to a portion of at least 18 consecutive nucleotides of SEQ ID NO: 10 and a second strand complementary to the first strand, that is complementary to an aphid gene that encodes a sucrase protein, dissolving the dsRNA to form a solution, and contacting an effective amount of said solution to an aphid species, wherein said solution is ingested by said aphid species and RNA interference is induced, resulting in mortality of said aphid.

3. The method of claim 2, wherein the double stranded ribonucleic acid construct is dissolved in a sucrose solution.

4. The method of claim 2, wherein the double stranded ribonucleic acid construct is dissolved in water.

5. The method of claim 2, wherein the solution is applied to aphid bait material.

6. The method of claim 2, wherein the solution further comprises a surfactant.

7. The method of claim 2, wherein the solution further comprises a virus-induced gene silencing (VIGS) vector.

8. The method of claim 2, wherein the effective amount of double stranded ribonucleic acid is approximately 314 ng per µl.

9. The method of claim 2, wherein the aphid species is *Diuraphis noxia*, *Myzus persicae*, or *Schizaphis graminum*.

10. An aphid control solution comprising a dsRNA, the dsRNA comprising a first sequence with at least 95% sequence identity to a portion of at least 18 consecutive nucleotides of SEQ ID NO: 10 and a second strand complementary to the first strand, wherein the dsRNA is dissolved in a solution and the solution optionally comprises a surfactant, a virus-induced gene silencing (VIGS) vector, or both a surfactant and a VIGS vector.

\* \* \* \* \*